United States Patent [19]

Hill

[11] Patent Number: 5,929,219
[45] Date of Patent: Jul. 27, 1999

[54] 9-HYDRAZONE AND 9-AZINE ERYTHROMYCIN DERIVATIVES AND A PROCESS OF MAKING THE SAME

[75] Inventor: David R. Hill, Gurnee, Ill.

[73] Assignee: Abbott Laboratories, Abbott Park, Ill.

[21] Appl. No.: 08/927,057

[22] Filed: Sep. 10, 1997

[51] Int. Cl.[6] .............................. C07H 1/00; C12P 19/62
[52] U.S. Cl. ............................................. 536/7.2; 536/18.5
[58] Field of Search ...................... 536/7.2, 18.5

[56] References Cited

U.S. PATENT DOCUMENTS

| | | | |
|---|---|---|---|
| 4,331,803 | 5/1982 | Watanabe et al. | 536/7.2 |
| 4,668,776 | 5/1987 | Yamada et al. | 536/7.4 |
| 4,670,549 | 6/1987 | Morimoto et al. | 536/7.4 |
| 4,672,109 | 6/1987 | Watanabe et al. | 536/7.2 |
| 4,680,386 | 7/1987 | Morimoto et al. | 536/7.4 |
| 4,990,602 | 2/1991 | Morimoto et al. | 536/7.4 |
| 5,274,085 | 12/1993 | Amano et al. | 536/7.4 |

FOREIGN PATENT DOCUMENTS

0260938 A2   3/1988   European Pat. Off. .

OTHER PUBLICATIONS

Egan et al. J. Org. Chem. 39(17): 2492–2494, 1974.

*Primary Examiner*—Gary L. Kunz
*Attorney, Agent, or Firm*—Portia Chen; Mona Anand

[57] ABSTRACT

Disclosed are 9-hydrazone erythromycin and 9-azine erythromycin derivatives and the processes for making the same. The compounds are useful intermediates for conversion into 6-O-alkyl erythromycin. Also disclosed are the processes for converting the compounds into 6-O-alkyl erythromycin.

14 Claims, No Drawings

9-HYDRAZONE AND 9-AZINE ERYTHROMYCIN DERIVATIVES AND A PROCESS OF MAKING THE SAME

TECHNICAL FIELD

The present invention relates to 9-hydrazone and 9-azine erythromycin derivatives and a process of making the same. These compounds are useful intermediates in the process of preparing 6-O-alkyl erythromycin thereof.

BACKGROUND OF THE INVENTION

6-O-methylerythromycin A (clarithromycin), shown below, is a potent macrolide antibiotic disclosed in U.S. Pat. No. 4,331,803.

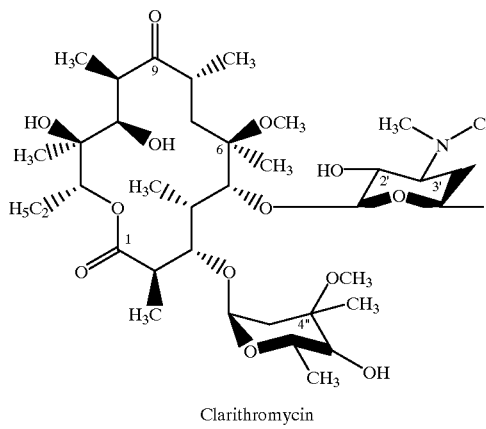

Clarithromycin

In general, the process for making clarithromycin can be thought of as a four-step procedure beginning with erythromycin A as the starting material:

Step 1: optionally convert the 9-oxo group to an oxime;
Step 2: protect the 2' and 4" hydroxyl groups;
Step 3: methylate the 6-hydroxyl group; and
Step 4: deprotect at the 2', 4" and 9-positions.

A variety of means for preparing 6-O-methylerythromycin A have been described. 6-O-methylerythromycin A can be prepared by methylating a 2'-O-3'-N-dibenzyloxycarbonyl-des-N-methyl derivative of erythromycin A (U.S. Pat. No. 4,331,803). 6-O-methylerythromycin A can also be made from 9-oxime erythromycin A derivatives (See, e.g., U.S. Pat. Nos. 5,274,085; 4,680,386; 4,668,776; 4,670,549 and 4,672,109, U.S. Pat. No. 4,990,602 and European Patent Application 0260938 A2).

In those reports relating to 9-oxime erythromycin A derivatives, the oxime is protected during methylation with a 2-alkenyl group (U.S. Pat. Nos. 4,670,549 and 4,668,776), a benzyl or substituted benzyl group (U.S. Pat. Nos. 4,680,386, and 4,670,549) or a moiety selected from the group consisting of lower alkyl, substituted alkyl, lower alkenyl, aryl substituted methyl, substituted oxalkyl, substituted thiomethyl (U.S. Pat. No. 4,672,109), and ketal group (U.S. Pat. No. 4,990,602).

There continues to be a need to provide a rapid, efficient method of producing 6-O-alkyl erythromycin compounds that uses mild, neutral synthetic conditions and to provide novel intermediates useful in the production of 6-O-alkyl erythromycin derivatives.

SUMMARY OF THE INVENTION

The invention relates to novel 9-hydrazone and 9-azine erythromycin derivatives, to a process of making the same, and their use as intermediates in the preparation of 6-O-alkyl erythromycin.

In one aspect, the present invention relates to a compound having the formula:

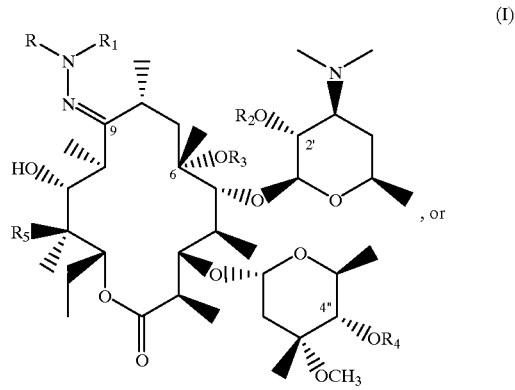

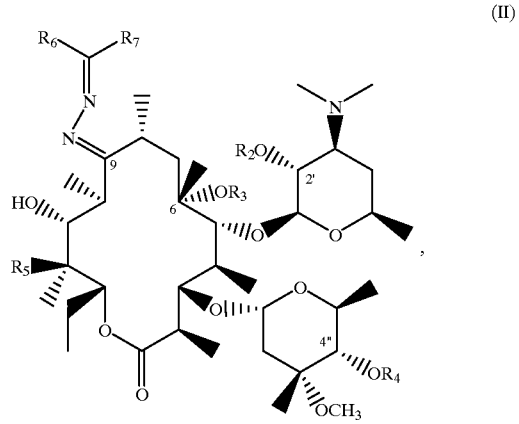

wherein R and $Rz_1$ are independently a hydrogen or a nitrogen-protecting group;

$R_2$ and $R_4$ are independently a hydrogen or a hydroxy-protecting group;

$R_3$ is a loweralkyl or aryl group;

$R_5$ is a hydrogen, hydroxy or a protected hydroxy group; and $R_6$ and $R_7$ are independently at each occurrence a hydrogen, an alkyl or an aryl group.

In another aspect, the present invention relates to a process for preparing a compound of the formula I, wherein the process comprises a) reacting an erythromycin of the formula I:

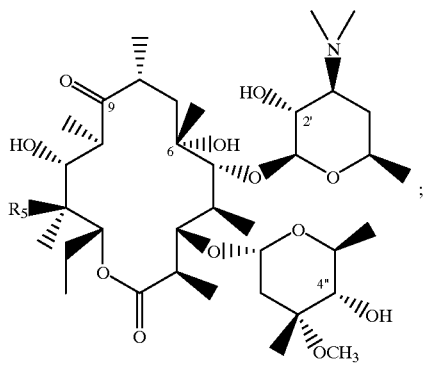
(III)

wherein $R_5$ is as defined above, with hydrazine to convert the 9-keto into a corresponding 9-hydrazone erythromycin;

b) protecting the 2'-hydroxy, and optionally protecting the 4"-hydroxy, and the amino nitrogen of the hydrazone with hydroxy and nitrogen protecting groups, respectively; and c) selectively alkylating the 6-hydroxy group.

In still another aspect, the present invention relates to a process for preparing a compound of the formula II, wherein the process comprises a) reacting an erythromycin of the formula III:

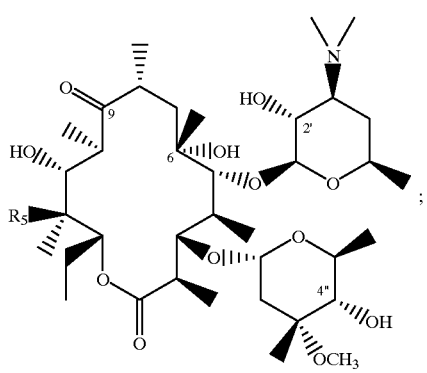
(III)

wherein $R_5$ is as defined above, with hydrazine to convert the 9-keto into a corresponding 9-hydrazone erythromycin;

b) reacting the hydrazone from step (a) with a ketone, an aldehyde or an acetal thereof or an ortho formate to produce a corresponding erythromycin 9-azine;

c) protecting the 2'-hydroxy and optionally protecting the 4"-hydroxy and the amino nitrogen of the 9-azine, with hydroxy-protecting and nitrogen-protecting groups, respectively; and d) selectively alkylating the 6-hydroxy group.

The compounds of the invention are useful as intermediates in the preparation of 6-O-alkyl erythromycins which are potent antibacterial compounds.

The process of converting the compound of formula (a) into 6-O-alkyl erythromycin comprises deprotecting the hydroxy and nitrogen protected groups or the compound.

Alternatively, the process of converting the compound of formula (II) into 6-O-alkyl erythromycin comprises reacting the compound with hydroxylamine to afford the corresponding oxime, followed by deprotection with sodium hydrogen sulfite; or reacting the compound with hydrazine to afford the corresponding hydrazone and followed by deprotection with nitrous acid.

DETAILED DESCRIPTION OF THE INVENTION

A number of defined terms are used herein to designate particular elements of the present invention.

The term "erythromycin derivatives" refers to erythromycin A or B having no substituent group or having conventional substituent groups, in organic synthesis, in place of the hydrogen atoms of the 2'-, and/or 4"-hydroxy groups.

The term "alkyl" refers to saturated, straight- or branched-chain hydrocarbon radicals containing between one and ten carbon atoms including, but not limited to, methyl, ethyl, propyl, isopropyl, n-butyl, tert-butyl and neopentyl.

The term "aryl" refers to a mono-, fused bicyclic or fused tricyclic carbocyclic ring system having one or more aromatic rings including, but not limited to, phenyl, naphthyl, tetrahydronaphthyl, phenanthrenyl, biphenylenyl, indanyl, indenyl and the like. The term "bicyclic aryl" as used herein includes naphthyl, tetrahydronaphthyl, indanyl, indenyl and the like. The term "tricyclic aryl" as used herein includes anthracenyl, phenanthrenyl, biphenylenyl, fluorenyl, and the like. Aryl groups (including bicyclic and tricyclic aryl groups) can be unsubstituted or substituted with one, two or three substituents independently selected from loweralkyl, haloalkyl, alkoxy, thioalkoxy, amino, alkylamino, dialkylamino, alkenyloxy, hydroxy, halo, mercapto, nitro, carboxaldehyde, carboxy, alkoxycarbonyl and carboxamide. Substituents also include methylenedioxy and ethylenedioxy. In addition, substituted aryl groups include tetrafluorophenyl and pentafluorophenyl.

The term "alkylaryl" refers to an aryl group having alkyl substituents attached to the aryl group.

The term "alkylating reagent" refers to a reagent capable of placing an alkyl group onto a nucleophilic site, including, but not limited to, alkyl halides such as methyl bromide, ethyl bromide, n-propyl bromide, methyl iodide, ethyl iodide, n-propyl bromide; dialkyl sulfates such as dimethyl sulfate, diethyl sulfate, di-n-propyl sulfate; and alkyl or aryl sulfonates such as methyl-p-toluenesulfonate, ethyl methanesulfonate, n-propyl methanesulfonate, methyl trifluoromethanesulfonate and the like.

The term "aryl(loweralkyl)" refers to a loweralkyl radical having appended thereto 1-3 aromatic hydrocarbon groups, as for example benzyl, diphenylbenzyl, trityl and phenylethyl.

The term "aryloxy" refers to an aromatic hydrocarbon radical which is joined to the rest of the molecule via an ether linkage (i.e., through an oxygen atom), as for example phenoxy.

The term "cycloalkyl" refers to a saturated monocyclic hydrocarbon radical having from three to eight carbon atoms in the ring and optionally substituted with between one and three additional radicals selected from among loweralkyl, halo(loweralkyl), loweralkoxy, halogen. Examples of cycloalkyl radicals include, but are not limited to, cyclopropyl, cyclobutyl, cyclopentyl, cyclohexyl, cycloheptyl, 1-fluoro-cyclopropyl, 2-fluorocyclopropyl and 2-aniinocyclopropyl.

The term "hydroxy-protecting group" is well-known in the art and refers to substituents on functional hydroxy groups of compounds undergoing chemical transformation which prevent undesired reactions and degradations during a synthesis (see, for example, T. H. Greene and P. G. M. Wuts, Protective Groups in Organic Synthesis, 2nd edition, John Wiley & Sons, New York (1991)). Examples of hydroxy-protecting groups include, but are not limited to, benzyloxycarbonyl, acetyl, or a substituted silyl group of formula $SiR^8R^9R^{10}$, wherein $R^8$, $R^9$ and $R^{10}$ are the same or different and each is a hydrogen atom, a loweralkyl group, a phenyl-substituted alkyl group in which the alkyl moiety has 1 to 3 carbon atoms, a phenyl group, a cycloalkyl group having 5 to 7 carbon atoms, or a loweralkenyl group having 2 to 5 carbon atoms and wherein at least one of $R^8$, $R^9$ and $R^{10}$ is not a hydrogen atom; and the like The term "loweralkenyl" refers to a straight- or branched-chain hydrocarbon radical containing between two and six carbon atoms and possessing at least one carbon-carbon double bond. Examples of loweralkenyl radicals include vinyl, allyl, 2- or 3-butenyl, 2-,3- or 4-pentenyl, 2-,3-,4- or 5-hexenyl and isomeric forms thereof.

The term "loweralkoxy" refers to an loweralkyl radical which is joined to the rest of the molecule via an ether linkage (i.e., through an oxygen atom). Examples of loweralkoxy radicals include, but are not limited to, methoxy and ethyloxy.

The term "loweralkyl" refers to an alkyl radical containing one to six carbon atoms including, but not limited to, methyl, ethyl, propyl, isopropyl, n-butyl, tert-butyl and neopentyl.

The term "substituted alkylaryl" refers to an alkylaryl group as defined above, substituted with substituents such as nitro, alkyl, amino, halo, alkoxy as defined above, and the like.

The term "protected hydroxy" refers to a hydroxy group protected with a hydroxy protecting group, as defined above.

The term "polar aprotic solvent" refers to polar organic solvents lacking an easily removed proton, including, but not limited to, N,N-dimethyl-formamide, dimethyl sulfoxide, N-methyl-2-pyrrolidone, hexamethyl-phosphoric triamide, tetrahydrofuran, 1,2-dimethoxyethane, acetonitrile or ethyl acetate, and the like.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heteroaryl compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. 11, in the Techniques of Chemistry Series, John Wiley & Sons, NY, 1986.

The term "strong alkali metal base" refers to an alkali metal base having a weak conjugate acid, including, but not limited to, sodium hydroxide, potassium hydroxide, sodium hydride, potassium hydride, potassium t-butoxide, and the like.

The term "substituted aryl(loweralkyl)" refers to an aryl (loweralkyl) residue as defined above having between one and three non-hydrogen ring substituents, each independently selected from among halogen, loweralkoxy, loweralkyl, hydroxy-substituted loweralkyl, and (loweralkyl)amino. Examples of substituted aryl (loweralkyl) radicals include 2-fluorophenylmethyl, 4-fluorophenylethyl and 2,4-difluorophenylpropyl.

The compounds of the invention are represented by:

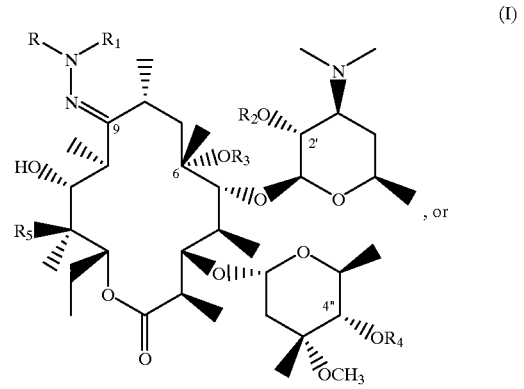

(I)

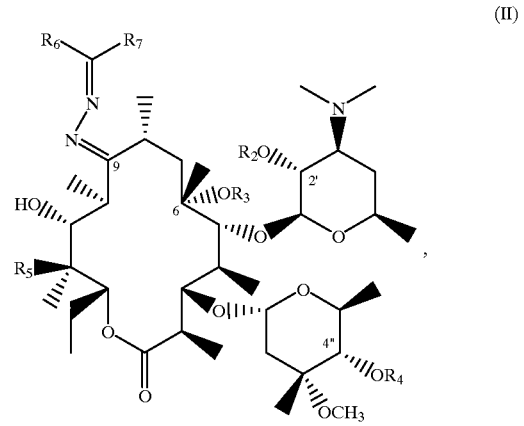

(II)

wherein R and $R_1$ are independenty a hydrogen or a nitrogen-protecting group;

$R_2$ and $R_4$ are independently a hydrogen or a hydroxy-protecting group;

$R_3$ is a loweralkyl or an aryl group;

$R_5$ is a hydrogen, hydroxy or a protected hydroxy group; and $R_6$ and $R_7$ are independently at each occurrence a hydrogen, an alkyl or an aryl group.

Representative of the preferred compounds of the invention, include, but are not limited to compounds of formula I, wherein $R_2$ and $R_4$ are trimethylsilyl groups, $R_5$ is hydroxyl, $R_3$ is methyl and R and $R_1$ are independently hydrogen and triisopropylsilyl groups; and $R_2$ and $R_4$ are trimethylsilyl groups, $R_5$ is hydroxyl, $R_3$ is methyl and R and $R_1$ are independently hydrogen and t-butyldimethylsilyl groups.

Representative of the preferred compounds of the invention, also include, but are not limited to compounds of formula II;

wherein $R_2$ and $R_4$ are trimethylsilyl groups, $R_5$ is hydroxyl, $R_3$ is methyl and R and $R_1$ are independently hydrogen and isopropylidene; and $R_2$ and $R_4$ are trimethylsilyl groups, $R_5$ is hydroxyl, $R_3$ is methyl and R and $R_1$ are independently hydrogen and cyclohexylidene.

The compounds of formula I are prepared by first converting the 9-keto group of an erythromycin A or B into erythromycin 9-hydrazone. The methods of preparing hydrazones are described in Sigal et al., *J. Am. Chem. Soc.,* 78, 388–395, (1956). As for example, the 9-hydrazone is prepared by heating erythromycin at reflux in an alcoholic solvent such as methanol, ethanol or isopropanol in the presence of hydrazine until no starting material remains. The reaction typically lasts from about 12 to 36 hours. The solvent is then removed and the crude solid so obtained is used without further purification.

The 2'- and optionally the 4"-hydroxy groups of the erythromycin 9-hydrazone are then protected with a hydroxy protecting groups, such as silyl, acyl and sulfonyl groups and the like, by the methods described in T. H. Greene and P. G. M. Wuts, Protective Groups in Organic Synthesis, 2nd edition, John Wiley & Sons, New York (1991). When the protecting group is a silyl group, both the 2'- and 4"-hydroxy groups are silylated. Preferably, the 2'- and 4"-hydroxy groups are protected with trimethylsilyl groups by treating a suspension of erythromycin 9-hydrazone in acetonitrile with hexamethyldisilazane at ambient temperature and stirred for 12–24 hours. The resulting solution is made basic by adding aqueous sodium hydroxide to adjust the pH typically ranging from 8–13, preferably, 9. The erythromycin 9-hydrazone derivative thus obtained is extracted into an aprotic solvent and the solvent evaporated to give the erythromycin 2',4"-bis-O-trimethylsilyl 9-hydrazone.

The amino nitrogen of the 9-hydrazone erythromycin derivative may optionally be protected by the nitrogen protecting groups by the methods described in T. H. Greene and P. G. M. Wuts, Protective Groups in Organic Synthesis, 2nd edition, John Wiley & Sons, New York, Chapter 7, (1991); and P. J. Kocienski, Protective Groups, Thieme, Chapter 6, (1994); and the references cited therein.

As for example, the amino nitrogen of the 9-hydrazone is protected by treating erythromycin 9-hydrazone with 1–2 equivalents of silylating agent such as triisopropylsilyl triflate in the presence of an organic base such as triethylamine in an aprotic solvent. Preferably, the reaction is carried out in the presence of triethylamine in dichloroethane. The reaction results in the formation of 9-(N-triisopropylsilyl) hydrazone erythromycin derivative which is protected at the 2'- and optionally at the 4"-positions. The hydrazone nitrogen may alternatively be protected by treating the 9-hydrazone with an appropriate ketal.

In another process of the invention, the erythromycin 9-hydrazone derivative is converted into an azine by the methods described in, for example, U.S. Pat. No. 3,780,020 and German Patent 1,966,310. As for example, the azine derivative is prepared by treating the hydrazone with an appropriate ketone, aldehyde or an acetal thereof or an orthoformate with or without a co-solvent and either with or without an added dehydrating agent such as molecular sieves. The reaction is carried out at a temperature between the room temperature and the boiling point of the ketone, aldehyde, or the co-solvent. The reaction is carried out for about one hour to about 24 hours. The azine nitrogen may be further protected by treating the 9-azine erythromycin derivative with an appropriate ketal in the presence of catalytic quantity of acid such as formic or acetic acid. The reaction mixture is stirred at ambient temperature overnight for 6 to 18 hours. The mixture is then basified to pH 8–13 and the product extracted into an appropriate solvent.

The alkylation of erythromycin 9-hydrazone derivative and erythromycin 9-azine-ketal derivative is achieved by reacting the starting compound with a suitable alkylating agent in the presence of a base. Typically, the reaction is carried out with an alkylating reagent in presence of a strong alkali metal base, in a suitable stirred or agitated polar aprotic solvent, or a mixture of such polar aprotic solvents maintained at a reaction temperature and for a period of time sufficient to effect alkylation, preferably from –15 C to room temperature for a period of one to 8 hours. The alkylating agents comprise methyl bromide, ethyl bromide, n-propyl bromide, methyl iodide, ethyl iodide, n-propyl bromide, dimethyl sulfate, diethyl sulfate, di-n-propyl sulfate, methyl-p-toluenesulfonate, ethyl methanesulfonate, methyl trifluoromethanesulfonate and n-propyl methanesulfonate. The amount of alkylating agent used is from zI to 3 molar equivalents relative to the 3'-N-oxide compound. The alkali metal base is selected from the group consisting of an alkali metal hydride, alkali metal hydroxide or alkali metal alkoxide. Examples of the alkali metal base include sodium and potassium hydride, sodium and potassium hydroxide and potassium t-butoxide. The amount of the base used is usually 1 to 2 equivalents relative to the starting compound.

The deprotection of the erythromycin 6-O-alkylated 9-hydrazone or 9-azine derivatives is carried out by the methods known in the art to obtain the erythromycin 6-O-alkylated 9-hydrazone or 9-azine. By way of an example, where the 2'- and 4"-positions are silylated, the silyl group can be removed by reacting the silylated derivative with formic acid in isopropanol. The silyl group can also be removed by using n-tetrabutylammonium fluoride in tetrahydrofuran, acetic acid, tetrahydrofuran and water, citric acid and methanol, Dowexz® resin and methanol, potassium carbonate and methanol, n-tetrabutylammonium chloride and potassium fluoride or hydrofluoric acid and acetonitrile. In the cases where the 9-hydrazone hydrogen is protected with a silyl group, removal of the silyl group is accomplished using the same procedure as set forth above.

In the alternative process, where the 9-hydrazone is converted into 9-azine, the 9-azine is removed by treating the 9-azine derivative with hydroxylamine or with hydrazine at an appropriate temperature and for a period of time sufficient to effect complete transformation. The reaction is carried out at a temperature from room temperature to 100° C. for a period of 12 to 24 hours. When treated with hydroxylamine, the resulting oxime is deprotected by methods well known in the art, preferably, by refluxing with sodium hydrogen sulfite in alcohol.

When treated with hydrazone, the resulting unsubstituted 9-hydrazone group is removed by methods known to those skilled in the art, preferably, by treating the hydrazone with nitrous acid in an aqueous/organic solution. The 6-O-alkyl erythromycin thus obtained is extracted from the aqueous solution after basification to pH 8–13.

Abbreviations

Certain abbreviations are used repeatedly in the specification which follows. These include: DMSO for dimethyl sulfoxide; HPLC for high performance liquid chromatography; IPCH ketal for isopropyl cyclohexyl ketal; TEA for triethylamine; TzEME for t-butyl methyl ether; TBAF for n-tetrabutylammonium fluoride; MeCN for acetonitrile, THF for tetrahydrofuran; HMDS for hexamethyldisilazane; and TMS for trimethylsilyl.

The invention may be better understood by reference to the following examples which are presented for illustration and not to limit the scope of the inventive concept

EXAMPLE 1

Example 1(a)
Erythromycin A 9-hydrazone

Erythromycin A (50 g) was dissolved in anhydrous methanol (150 mL) by gentle warming. To this solution was added a solution of 12.5 g anhydrous hydrazine in 50 mL of methanol. The mixture was heated at reflux for 24 hours with the exclusion of moisture from the air. The methanol and excess hydrazine were removed by evaporation under reduced pressure leaving an amorphous white solid which was crystallized from aqueous isopropanol to give the product (31 g).

Example 1(b)
Erythromycin A 2',4"-bis-O-trimethylsilyl-9-hydrazone

Erythromycin A 9-hydrazone (50 g) was suspended in acetonitrile. Formic acid (10 ml) and hexamethyldisilazane (55 g) were added sequentially below 20° C. The mixture was stirred at ambient temperature overnight. The resulting solution was cooled with an ice bath and then rendered basic (pH>9) with aqueous NaOH. The mixture was extracted with heptane and the heptane layer separated and dried ($Na_2SO_4$). Evaporation in vacuo gave a white solid (40 g), characterized by the NMR and mass spectra.

$^1$Hnmr (500 MHz, $CDCl_3$), d: 2.66 (1H, H2), 1.15 (3H, C2C$\underline{H}_3$), 4.26 (1H, C3C$\underline{H}$), 1.86 (1H, H4), 1.06 (C4C$\underline{H}_3$), 3.50 (1H, C5C$\underline{H}$), 1.41 (3H, C6C$\underline{H}_3$), 1.63, 1.41 (2H, C'7C$\underline{H}_2$), 3.31 (1H, C8C$\underline{H}$), 1.06 (3H, C8C$\underline{H}_3$), 2.63 (1H, C10C$\underline{H}$), 1.11 (3H, C10C$\underline{H}_3$), 3.39 (1H, C11C$\underline{H}$), 1.13 (3H, C12C$\underline{H}$3), 5.00 (1H, C13C$\underline{H}$, 1.90, 1.44 (2H, C14C$\underline{H}_2$), 0.83 (3H, C15C$\underline{H}_3$), 4.37 (1H, C1'C$\underline{H}$), 3.16 (1H, C2'C$\underline{H}$), 2.48 (1H, C3'C$\underline{H}$), 2.21 (6H, C3'N(C$\underline{H}_3$)$_2$), 1.62, 1.15 (2H, C4'C$\underline{H}_2$), 3.59 (1H, C5'C$\underline{H}$), 1.13 (3H, C6'C$\underline{H}_3$), 4.89 (1H, C1"C$\underline{H}$), 2.36, 1.46 (2H, C2"C$\underline{H}_2$), 3.27 (3H, C3"OC$\underline{H}_3$), 1.12 (3H, C3"C$\underline{H}_3$), 3.13 (1H, C4"C$\underline{H}$), 4.25 (1H, C5"C$\underline{H}$), 1.19 (3H, C6"C$\underline{H}_3$), 0.12 (9H, 4"OTMS), 0.08 (9H, 2'OTMS), 3.23 (1H, 6OH), 3.18 (1H, 12OH). $^{13}$Cnmr (125MHz, $CDCl_3$), d: 176.6 (C=O), 44.8 (C2), 15.1 (C2Me), 79.2 (C3), 42.0 (C4), 10.0 (C4Me), 81.8 (C5), 75.6 (C6), 27.1 (C6Me), 39.0 (C7), 26.1 (C8), 19.0 (C8Me), 167.2 (C9, C=N), 33.2 (C10), 13.6 (C10Me), 71.1 (C11), 74.2 (C12), 16.1 (C12Me), 77.1 (C13), 21.2 (C14), 10.8 (C15), 102.9 (C1'), 73.2 (C2'), 65.2 (C3'), 40.9 (C3'NMe), 30.0 (C4'), 68.1 (C5'), 21.4 (C6'), 97.2 (C$^{1"}$), 35.7 (C2"), 73.1 (C3"), 49.6 (C3"OMe), 22.0 (C3"Me), 80.7 (C4"), 65.1 (C5"), 19.1 (C6"), 0.8 (C2'OTMS), 0.8 (C4"OTMS). MS (m/z): FAB 892 [M+H]$^+$

Example 1(c)
Erythromycin 2',4"-bis-O-trimethylsilyl-9-(N-triisopropylsilyl) hydrazone Erythromycin A 2',4"-bis-O-trimethylsilyl-9-hydrazone (1.5 g) was dissolved in $CH_2Cl_2$ and TEA (0.5 ml) was added followed by triisopropylsilyl triflate (0.67 ml). The resulting mixture was stirred at ambient temperature for 2 h. Evaporation in vacuo gave an oil which was partitioned between TBME and water. The organic layer was separated and washed with water, then dried ($Na_2SO_4$) and evaporated in vacuo to give a white solid 1.6 g; 91%. $^1$Hnmr (500 MHz, $CDCl_3$), d: 2.63 (1H, H2), 1.16 (3H, C2C$\underline{H}_3$), 4.21 (1H, C3C$\underline{H}$), 1.83 (1H, H4), 1.05 (C4C$\underline{H}_3$), 3.46 (1H, C5C$\underline{H}$), 1.35 (3H, C6C$\underline{H}_3$), 1.58, 1.38 (2H, C7C$\underline{H}_2$), 3.32 (1H, C8C$\underline{H}$), 1.10 (3H, C8C$\underline{H}_3$), 2.64 (1H, C10C$\underline{H}$), 1.10 (3H, C10C$\underline{H}_3$), 3.45 (1H, C11C$\underline{H}$), 1.16 (3H, C12C$\underline{H}_3$), 4.98 (1H, C13C$\underline{H}$), 1.91, 1.42 (2H, C14C$_2$), 0.86 (3H, C15C$\underline{H}_3$), 4.45 (1H, C1'C$\underline{H}$), 3.20 (1H, C2'CH), 2.54 (1H, C3'CH), 2.25 (6H, C3'N(C$\underline{H}_3$)2), 1.65, 1.16 (2H, C4'C$\underline{H}_2$), 3.67 (1H, C5'C$\underline{H}$), 1.16 (3H, C6'C$\underline{H}_3$), 4.88 (1H, C1"C$\underline{H}$), 2.36, 1.46 (2H, C2"C$\underline{H}_2$), 3.28 (3H, C3"OC$\underline{H}_3$), 1.12 (3H, C3"C$\underline{H}_3$), 3.13 (1H, C4"C$\underline{H}$), 4.21 (1H, C5"C$\underline{H}$, 1.16 (3H, C6"C$\underline{H}_3$), 0.13 (9H, 4"OTMS), 0.10 (9H, 2'OTMS), 3.23 (1H, 12OH), 4.94 (1H, 11OH), 5.56 (1H, =N-NH-), 1.16, 1.04 (1H&3H, CH&CH$_3$ of iso-Pr).

$^{13}$Cnmr (125MHz, $CDCl_3$), d: 176.5 (C=O), 44.8 (C2), 14.5 (C2Me), 78.3 (C3), 42.9 (C4), 10.1 (C4Me), 82.8 (C5), 74.9 (C6), 25.6 (C6Me), 40.1 (C7), 24.6 (C8), 19.0 (C8Me), 158.7 (C9, $\underline{C}$=N), 33.4 (C10), 13.6 (C10Me), 72.2 (C11), 74.3 (C12), 16.4 (C12Me), 77.5 (C13), 21.7 (C14), 11.0 (C15), 102.5 (C1'), 73.1 (C2'), 65.3 (C3'), 40.9 (C3'NMe), 29.9 (C4'), 68.0 (C5'), 21.4 (C6'), 96.4 (C1"), 35.5 (C2"), 73.2 (C3"), 49.4 (C3"OMe), 22.2 (C3"Me), 80.7 (C4"), 65.0 (C5"), 19.1 (C6"), 0.9 (C2'OTMS), 0.8 (C4"OTMS), 18.2, 18.1, 17.7, 11.4 (iso-Pr).

MS (m/z): FAB1048 [M+H]+, FAB+KI 1086 [M+K]$^+$

Example 1 (d)
Erythromycin A 2'4"-bis-O-timethylsilyl-6-O-methyl-9-(N-triisopropvlsilyl) hydrazone Erythromycin A 2',4"-bis-O-trimethylsilyl-9-(N-triisopropylsilyl) hydrazone (1.2 g, 1.146 mmol) was dissolved in a 1:1 mixture of DMSO and THF (10 ml) and the solution cooled to 5° C. Methyl iodide (0.43 ml; 6.9 mmol; 6eq) was added followed by KOH (0.26 g; 4.58 mmol; 4 eq). The resulting mixture was stirred at 5° C for lh the quenched by adding 40% aq. methylamine (1 ml) and the mixture stirred for 10 min. Saturated NaCl (20 ml) was added and the mixture was extracted with TBME. The organic layer was separated and washed with saturated NaCl solution, then dried ($Na_2SO_4$) and evaporated in vacuo to give a white solid 1.18 g; 97%.

$^1$Hnmr (500 MHz, $CDCl_3$), d: 2.90 (1H, H2), 1.20 (3H, C2C$\underline{H}_3$), 3.76 (1H, C3C$\underline{H}$), 1.90 (1H, H4), 1.08 (C4C$\underline{H}_3$), 3.71 (1H, C5C$\underline{H}$), 1.41 (3H, C6C$\underline{H}_3$), 3.14 (3H, C6OC$\underline{H}_3$), 1.60, 1.53 (2H, C7C$\underline{H}_2$), 3.06 (1H, C8C$\underline{H}$), 0.97 (3H, C8C$\underline{H}_3$), 2.52 (1H, C10C$\underline{H}$), 1.08 (3H, C10C$\underline{H}_3$), 3.67 (1H, C11C$\underline{H}$), 1.18 (3H, C12C$\underline{H}_3$), 5.14 (1H, C13C$\underline{H}$), 1.94, 1.46 (2H, C14C$\underline{H}_2$), 0.83 (3H, C15C$\underline{H}_{13}$), 4.46 (1H, C1'C$\underline{H}$), 3.14 (1H, C2'C$\underline{H}$), 2.52 (1H, C3'C$\underline{H}$), 2.22 (6H, C3'N(C$\underline{H}_{3)2}$), 1.65, 1.13 (2H, C4'C$\underline{H}_2$), 3.67 (1H, C5'CH), 1.18 (3H, C6'C$\underline{H}_3$), 4.91 (1H, C1"C$\underline{H}$), 2.35, 1.49 (2H, C2"C$\underline{H}_2$), 3.31 (3H, C3"OC$\underline{H}_3$), 1.18 (3H, C3"C$\underline{H}_3$), 3.16 (1H, C4"C$\underline{H}$), 4.23 (1H, C5"C$\underline{H}$), 1.22 (3H, C6"C$\underline{H}_3$), 0.2 (9H, 4"OTMS), 0.10 (9H, 2'OTMS), 3.37 (1H, 12OH), 5.25 (1H, 11OH), 5.28 (1H,=N-NH-), 1.19, 1.08 (1H&3H, CH&CH$_3$ of iso-Pr).

$^{13}$Cnmr (125 MHz, $CDCl_3$), d: 175.4 (C=O), 45.2 (C2), 16.2 (C2 Me), 78.2 (C3), 38.8 (C4), 9.9 (C4 Me), 78.6 (C5), 78.7 (C6), 51.7 (C60Me), 20.7 (C6 Me), 37.7 (C7), 24.0 (C8), 19.2 (C8 Me), 158.9 (C9, $\underline{C}$=N), 32.6 (C10), 14.9 (C10 Me), 71.1 (C11), 74.0 (C12), 16.0 (C12 Me), 76.7 (C13), 21.2 (C14), 10.4 (C15), 102.3 (C1'), 73.4 (C2'), 65.2 (C3'), 41.0 (C3'NMe), 29.5 (C4'), 67.0 (C5'), 22.0 (C6'), 96.2 (C1"), 35.9 (C2"), 73.1 (C3"), 49.6 (C3"OMe), 22.2 (C3"Me), 80.8 (C4"), 65.3 (C5"), 19.5 (C6"), 1.0 (C2'OTMS), 0.9 (C4"OTMS), 18.2, 17.9, 11.4 (iso-Pr). MS (mz/z):, FAB 1062 [M+H]$^+$

EXAMPLE 2

Example 2(a)
Erythromycin A 2',4"-bis-O-timethylsilyl-9-(N-tert-butyldimethylsilyl) hydrazone.

Erythromycin A 2',4"-bis-O-trimethylsilyl-9-hydrazone (1.5 g) from Example 1(b) was dissolved in $CH_2CL_2$ and TEA (0.5 ml) was added followed by tert-butyldimethylsilyl triflate (0.7 ml). The resulting mixture was stirred at ambient temperature for 2h. Evaporation in vacuo gave an oil which was partitioned between TBME and water. The organic layer was separated and washed with water, then dried ($Na_2SO_4$) and evaporated in vacuo to give a white solid 1.61 g; 95%.
$^1$Hnmr (500 MHz, $CDCl_3$), d: 2.65 (1H, H2), 1.18 (3H, C2C$\underline{H}_3$), 4.15 (1H, C3C$\underline{H}$), 1.82 (1H, H4), 1.06 (C4C$\underline{H}_3$), 3.48 (1H, C5C$\underline{H}$), 1.34 (3H, C6C$\underline{H}_3$), 1.57, 1.42 (2H, C7C$\underline{H}_2$), 3.29 (1H, C8C$\underline{H}$), 1.12 (3H, C8C$\underline{H}_3$), 2.68 (1H, C10 C$\underline{H}$), 1.12 (3H, C10C$\underline{H}_3$), 3.48 (1H, C11C$\underline{H}$), 1.18 (3H, C12C$\underline{H}_3$), 4.99 (1H, C13C$\underline{H}$), 1.94, 1.49 (2H, C14C$\underline{H}_2$), 0.89 (3H, C15C$\underline{H}_3$), 4.49 (1H, C1'C$\underline{H}$), 3.23 (1H, C2'C$\underline{H}$), 2.53 (1H, C3'C$\underline{H}$), 2.24 (6H, C3'N(C$\underline{H}_3$)2), 1.66, 1.21 (2H, C4'C$\underline{H}_2$), 3.71 (1H, C5'C$\underline{H}$, 1.18 (3H, C6'C$\underline{H}_3$), 4.94 (1H, C1"C$\underline{H}$), 2.38, 1.49 (2H, C2"C$\underline{H}_2$), 3.30 (3H, C3"OC$\underline{H}_3$), 1.15 (3H, C3"C$\underline{H}_3$), 3.16 (1H, C4"C$\underline{H}$), 4.22 (1H, C5"C$\underline{H}$), 1.18 (3H, C6"C$\underline{H}_3$), 0.15 (9H, 4"OTMS), 0.11 (9H, 2'OTMS), 3.23 (1H, 12OH), 4.94 (1H, l11OH), 5.54 (1H, =N-NH-), 0.16, 0.06 (6H, N-N-Si-(CH$_3$)$_2$), 0.91 (9H, N-Si-(C$\underline{H}_3$)$_3$).
$^{13}$Cnmr (125 MHz, $CDCl_3$), d: 176.6 (C=O), 44.6 (C2), 14.3 (C2 Me), 78.0 (C3), 42.9 (C4), 10.2 (C4 Me), 83.1 (C5), 74.8 (C6), 24.8 (C6 Me), 40.8 (C7), 24.8 (C8), 18.8 (C8 Me), 158.1 (C9, C=N), 33.5 (C10), 13.5 (C10 Me), 72.2 (Cl 11), 74.3 (C12), 16.4 (C12 Me), 77.7 (C13), 21.8 (C14), 11.2 (C15), 102.4 (C1'), 73.0 (C2'), 65.3 (C3'), 41.0 (C3'NMe), 29.7 (C4'), 67.9 (C5'), 21.6 (C6'), 96.0 (C1"), 35.4 (C2"), 73.2 (C3"), 49.4 (C3"OMe), 22.3 (C3"Me), 80.6 (C4"), 65.0 (C5"), 19.1 (C6"), 0.9 (C2'OTMS), 0.9 (C4"OTMS), 5.6, 5.9 (N-N-Si-(CH$_3$)$_2$), 18.1 (-N-Si-C), 26.4 (-N-Si-C(CH$_3$)$_3$). MS (m/z): FAB1006 [M+H]$^+$ Example 2(b)
Erythromycin A 2',4"-bis-O-trimethylsilyl-6-O-methyl-9-(N-tert-butyldimethylsilyl) hydrazone
Erythromycin A 2',4"-bis-O-trimethylsilyl-9-(N-tert-butyldimethylsilyl) hydrazone (1.2 g, 1.193 mmol) was dissolved in a 1:1 mixture of DMSO and THF (10 ml) and the solution cooled to 5° C. Methyl iodide (0.45 ml; 7.157 mmol; 6eq) was added followed by KOH (0.267 g; 4.77 mmol; 4eq). The resulting mixture was stirred at 5° C. for 1h then quenched by adding 40% aq. methylamine (1 ml) and the mixture stirred for 10 min. Saturated NaCl (20 ml) was added and the mixture was extracted with TBME. The organic layer was separated and washed with saturated NaCl solution, then dried ($Na_2SO_4$) and evaporated in vacuo to give a white solid 1.215 g; 99.9%.
$^1$Hnmr (500 MHz, $CDCl_3$), d: 2.89 (1H, H2), 1.19 (3H, C2C$\underline{H}_3$), 3.75 (1H, C3C$\underline{H}$), 1.88 (1H, H4), 1.06 (C4C$\underline{H}_3$), 3.68 (1H, C5C$\underline{H}$), 1.39 (3H, C6C$\underline{H}_3$), 3.10 (3H, C6OC$\underline{H}_3$), 1.58, 1.52 (2H, C7C$\underline{H}_2$), 2.99 (1H, C8C$\underline{H}$), 0.97 (3H, C8C$\underline{H}_3$), 2.49 (1H, C10C$\underline{H}$), 1.10 (3H, C10C$\underline{H}_3$), 3.66 (1H, C11C$\underline{H}$), 1.16 (3H, C12C$\underline{H}_3$), 5.12 (1H, C13C$\underline{H}$), 1.94, 1.48 (2H, C14C$\underline{H}_2$), 0.83 (3H, C15C$\underline{H}_3$), 4.45 (1H, Cl'C1'C$\underline{H}$), 3.14 (1H, C2'C$\underline{H}$), 2.51 (1H, C3'C$\underline{H}$), 2.22 (6H, C3'N(C$\underline{H}_3$)$_2$), 1.65, 1.16 (2H, C4'C$\underline{H}_2$), 3.66 (1H, C5'C$\underline{H}$), 1.16 (3H, C6'C$\underline{H}_3$), 4.91 (1H, C1"C$\underline{H}$), 2.35, 1.51 (2H, C2"C$\underline{H}_2$), 3.31 (3H, C3"OC$\underline{H}_3$), 1.16 (3H, C3"C$\underline{H}_3$), 3.16 (1H, C4"C$\underline{H}$), 4.23 (1H, C5"C$\underline{H}$), 1.22 (3H, C6"C$\underline{H}_3$), 0.09 (9H, 4"OTMS), 0.15 (9H, 2'OTMS), 3.38 (1H, 12OH), 5.46 (1H, 11OH), 5.20 (1H, =N-NH-), 0.16, 0.07 (6H, N-N-Si-(CH$_3$)$_2$), 0.92 (9H, N-Si-(C$\underline{H}_3$)$_3$).
$^{13}$Cnmr (125 MHz, $CDCl_3$), d: 175.5 (C=O), 45.2 (C2), 16.2 (C2 Me), 78.2 (C3), 38.8 (C4), 9.9 (C4 Me), 78.7 (C5), 78.7 (C6), 20.8 (C6 Me), 51.6 (C6OMe), 39.9 (C7), 24.0 (C8), 19.1 (C8 Me), 158.5 (C9, C=N), 32.4 (C10), 15.0 (C10 Me), 71.2 (C11), 73.9 (C12), 16.0 (C12 Me), 76.8 (C13), 21.1 (C14), 10.4 (C15), 102.4 (C1"), 73.4 (C2'), 65.2 (C3'), 41.1 (C3'NMe), 29.5 (C4'), 67.1 (C5'), 22.0 (C6'), 96.2 (C1"), 35.9 (C2"), 73.1 (C3"), 49.6 (C3"OMe), 22.0 (C3"Me), 80.8 (C4"), 65.3 (C5"), 19.5 (C6"), 0.9 (C2'OTMS), 0.9 (C4"OTMS), 5.3, 5.7 (N-N-Si-(CH$_3$)$_2$), 18.0 (-N-Si-C), 26.2 (-N-Si-C(CH$_3$)$_3$). MS (m/z): FAB1020 [M+H]+, FAB+KI 1058 [M+K]$^+$ Example 2(c)
Erythromycin A 6-O-methyl-9-hydrazone
Erythromycin A 2',4"-bis-O-trimethylsilyl-6-O-methyl-9-(N-tert-butyldimethylsilyl) hydrazone (500 mg; 0.49 mmol) was dissolved in THF and 1 M TBAF (2.5 ml; 2.5 mmol, 5.1 eq) was added. The mixture was stirred at ambient temperature for 1h, then evaporated in vacuo. The resulting oil was partitioned between i-PrOAc and water. The organic layer was separated and dried with $Na_2SO_4$ and evaporated in vacuo to give a white solid 300 mg; 80%. $^1$Hnmr (500 MHz, $CDCl_3$), d: 2.95 (1H, H$_2$), 1.20 (3H, C2C$\underline{H}_3$), 3.71 (1H, C3C$\underline{H}$), 1.96 (1H, H4), 1.11 (C4C$\underline{H}_3$), 3.78 (1H, C5C$\underline{H}$), 1.44 (3H, C6C$\underline{H}_3$), 3.19 (3H, C6OC$\underline{H}_3$), 1.65, 1.54 (2H, C7C$\underline{H}_2$), 3.16 (1H, C8C$\underline{H}$), 0.99 (3H, C8C$\underline{H}_3$), 4.91 (2H, N-NH$_2$), 2.54 (1H, C10C$\underline{H}$), 1.11 (3H, C10C$\underline{H}_3$), 3.51 (1H, C11C$\underline{H}$), 1.10 (3H, C12C$\underline{H}_3$), 5.10 (1H, C13C$\underline{H}$), 1.92, 1.47 (2H, C14C$\underline{H}_2$), 0.82 (3H, C15C$\underline{H}_3$), 4.50 (1H, C1'C$\underline{H}$), 3.18 (1H, C2'C$\underline{H}$), 3.44 (1H, C2'OH), 2.41 (1H, C3'C$\underline{H}$), 2.27 (6H, C3'N(C$\underline{H}_3$)$_2$), 1.64, 1.20 (2H, C4'C$\underline{H}_2$), 3.50 (1H, C5'C$\underline{H}$), 1.22 (3H, C6'C$\underline{H}_3$), 4.95 (1H, C1"C$\underline{H}$), 2.36, 1.60 (2H, C2"C$\underline{H}_2$), 3.32 (3H, C3"OC$\underline{H}_3$), 1.25 (3H, C3"C$\underline{H}_3$), 3.02 (1H, C4"C$\underline{H}$), 2.19 (1H, C4'OH), 4.03 (1H, C5"C$\underline{H}$), 1.29 (3H, C6"C$\underline{H}_3$).
$^{13}$Cnmr (125 MHz, $CDCl_3$), d: 174.9 (C=O), 44.8 (C2), 16.3 (C2 Me), 78.8 (C3), 38.1 (C4), 9.4 (C4 Me), 79.2 (C5), 79.1 (C6), 20.5 (C6 Me), 51.7 (C6OMe), 37.6 (C7), 26.1 (C8), 19.1 (C8 Me), 167.7 (C9, C=N), 32.6 (C10), 14.5 (C10Me), 71.1 (C11), 74.0 (C12), 15.9 (C12 Me), 77.0 (C13), 21.0 (C14), 10.6 (C15), 102.3 (C1'), 71.1 (C2'), 65.5 (C3'), 40.2 (C3'NMe), 28.6 (C4'), 68.5 (C5'), 21.4 (C6'), 96.3 (C1"), 35.0 (C2"), 72.7 (C3"), 49.4 (C3"OMe), 21.5 (C3"Me), 77.9 (C4"), 65.9 (C5"), 18.6 (C6"). MS (m/z): FAB 762 [M+H]$^+$ Example 2(d)
6-O-Methyl Erythromycin A
Erythromycin A 6-O-methyl-9-hydrazone (2.0 g; 2.62 mmol) was suspended in MeCN (25 ml) and cooled to 0–5° C. In a separate flask, NaNO2 (0.54 g; 7.86 mmol) was dissolved in H$_2$O (5 ml) and dil. HCl added to achieve pH 4. The freshly prepared nitrous acid was added dropwise to the cooled suspension and the resulting mixture allowed to warm to room temperature. Additional dil. HCl was added to readjust the pH to ca. 4. The mixture was stirred at ambient temperature overnight. The resulting mixture was basified with 5% NaOH to pH>9 and extracted with MeCN. The organic layer was separated and washed with saturated NaCl solution, dried (MgSO4) and evaporated in vacuo to give a pale yellow solid (2 g) which was recrystallized from iso-PrOH to give a white solid.
$^1$Hnmr (500 MHz, $CDCl_3$), d: 2.89 (1H, H2), 1.20 (3H, C2C$\underline{H}_3$), 3.77 (1H, C3C$\underline{H}$), 1.92 (1H, H4), 1.10 (C4C$\underline{H}_3$), 3.67 (1H, C5C$\underline{H}$), 1.41 (3H, C6C$\underline{H}_3$), 3.04 (3H, C6OC$\underline{H}_3$), 1.85, 1.72 (2H, C7C$\underline{H}_2$), 2.59 (1H, C8C$\underline{H}$), 1.13 (3H, C8C$\underline{H}_3$), 3.00 (1H, C10C$\underline{H}$), 1.13 (3H, C10C$\underline{H}_3$), 3.77 (11H, C$\underline{H}$), 1.12 (3H, C12C$\underline{H}_3$), 5.05 (1H, C13C$\underline{H}$), 1.92, 1.47 (2H, C14C$\underline{H}_2$), 0.84 (3H, C15C$\underline{H}_3$), 4.44 (1H, C1'C$\underline{H}$), 3.19 (1H, C2'C$\underline{H}$), 2.42 (1H, C3'C$\underline{H}$), 2.29 (6H, C3'N(C$\underline{H}_3$)$_2$), 1.66, 1.22 (2H, C4'C$\underline{H}_2$), 3.49 (1H, C5'C$\underline{H}$), 1.23 (3H, C6'C$\underline{H}_3$), 4.93 (1H, C1"C$\underline{H}$), 2.37, 1.59 (2H, C2"C$\underline{H}_2$), 3.33 (3H, C3'OC$\underline{H}_3$), 1.25 (3H, C3"C$\underline{H}_3$), 3.03 (1H, C4"C$\underline{H}$), 4.01 (1H, C5"C$\underline{H}$), 1.31 (3H, C6"C$\underline{H}_3$).

¹³Cnmr (125 MHz, CDCl₃), d: 175.8 (C=O), 45.1 (C2), 15.9 (C2 Me), 78.4 (C3), 39.2 (C4), 9.1 (C4 Me), 80.8 (C5), 78.4 (C6), 19.7 (C6 Me), 39.3 (C7), 45.2 (C8), 18.0 (C8 Me), 220.9 (C9, C=O), 37.2 (C10 ), 12.3 (C10Me), 69.1 (C11), 74.3 (C12), 15.9 (C12 Me), 76.6 (C13), 21.0 (C14), 10.6 (C15), 102.7 (C1'), 71.0 (C2'), 65.6 (C3'), 40.3 (C3'NMe), 28.9 (C4'), 68.7 (C5'), 21.5 (C6'), 96.1 (C1"), 34.9 (C2"), 72.7 (C3"), 49.5 (C3"OMe), 21.4 (C3"Me), 77.9 (C4"), 65.8 (C5"), 18.7 (C6"). MS (m/z): FAB 748 [M+H]⁺

EXAMPLE 3

Example 3(a)

Erythromycin A 2',4"-bis-O-trimethylsilyl-9-isopropylidene azine

Erythromycin A 2',4"-bis-O-trimethylsilyl-9-hydrazone from Example 1(a) (2.0 g; 2.24 mmol) was dissolved in acetone (20 ml) and 3Åmolecular sieves (2 g) were added. The mixture was heated at reflux overnight, then diluted with MeCN. The sieves were removed by filtration though a pad of celite. The resulting solution was evaporated in vacuo to give a white solid (2 g).

¹Hnmr (500 MHz, CDCl₃), d: 2.86 (1H, H2), 1.15 (3H, C2CH₃), 4.18 (1H, C3CH), 1.94 (1H, H4), 1.10 (C4CH₃), 3.59 (1H, C5CH), 1.44 (3H, C6CH₃), 1.67, 1.49 (2H, C7CH₂), 3.53 (1H, C8CH), 1.04 (3H, C8CH₃), 2.76 (1H, C10CH), 1.22 (3H, C10CH₃), 3.71 (1H, C11CH), 1.18 (3H, C12CH₃), 5.10 (1H, C13CH), 1.92, 1.48 (2H, C14CH₂), 0.85 (3H, C15CH₃), 2.02, 1.86 (C17CH₃), 4.39 (1H, C1'CH), 3.18 (1H, C2'CH), 0.11 (9H, 2"OTMS), 2.53 (1H, C3'CH), 2.23 (6H, C3'N(CH₃)₂), 1.66, 1.18 (2H, C4'CH₂), 3.62 (1H, C5'CH), 1.17 (3H, C6'CH₃), 4.87 (1H, C1"CH), 2.35, 1.49 (2H, C2"CH₂), 3.30 (3H, C3"OCH₃), 1.15 (3H, C3"CH₃), 3.16 (1H, C4"CH), 0.14 (9H, 4"OTMS), 4.24 (1H, C5"CH), 1.22 (3H, C6"CH₃).

¹³Cnmr (125 MHz, CDCl₃), d: 175.5 (C=O), 44.7 (C2), 16.0 (C2 Me), 79.7 (C3), 39.7 (C4), 9.7 (C4 Me), 81.4 (C5), 75.5 (C6), 27.1 (C6 Me), 39.1 (C7), 29.3 (C8), 18.8 (C8 Me), 178.5 (C9, C=N), 33.1 (C10), 14.2 (C10 Me), 70.8 (C11), 74.4 (C12), 16.1 (C12 Me), 76.8 (C13), 21.1 (C14), 10.7 (C15), 163.5 (C16), 25.3, 18.3 (C17CH₃), 102.6 (C1'), 73.4 (C2'), 1.0 (C2'OSi(CH₃)₃), 65.2 (C3'), 41.0 (C3'NMe), 29.8 (C4'), 67.6 (C5'), 21.8 (C6'), 96.7 (C1"), 36.0 (C2"), 73.2 (C3"), 49.7 (C3"OMe), 22.2 (C3"Me), 80.9 (C4"), 0.9 (C4"OSi(CH₃)₃), 65.0 (C5"), 19.4 (C6"). MS (m/z): 932 [M+H]⁺

Example 3(b)

Erythromycin A 2', 4"-bis-O-trimethylsilyl-6-O-methyl-9-isopropylidene azine

Erythromycin A 2',4"-bis-O-trimethylsilyl-9-isopropylidene azine (1.0g; 1.07 mmol) from the above Example was dissolved in a 1:1 mixture of THF/DMS 0 (10 ml) and cooled to 5° C. Methyl iodide (0.40 ml; 6.44 mmol) and KOH (0.237 g; 4.23 mmol) were added and the mixture was stirred at 5° C for 4 hr. The reaction was quenched by the addition of aq methylarnine (1 ml). Saturated NaCl was added and the resulting mixture extracted with TBME. The organic layer was washed with saturated NaCl solution then dried (MgSO₄) and evaporated in vacuo to give a white solid 0.95 g (94%).

¹Hnmr (500 MHz, CDCl₃), d: 2.86 (1H, H₂), 1.18 (3H, C2CH₃), 3.77 (1H, C3CH), 1.84 (1H, H4), 1.05 (C4CH₃), 3.61 (1H, C5CH), 1.39 (3H, C6CH₃), 3.54 (1H, 6OMe), 1.59, 1.38 (2H, C7CH₂), 3.88 (1H, C8CH), 1.01 (3H, C8CH₃), 2.68 (1H, C10 CH), 1.20 (3H, C10CH₃), 3.78 (1H, C11CH), 1.19 (3H, C12CH₃), 5.10 (1H, C13CH), 1.95, 1.49 (2H, C14CH₂), 0.85 (3H, C15CH₃), 2.05, 1.95 (C17CH₃), 4.42 (1H, C1'CH), 3.13 (1H, C2'CH), 0.10 (9H, 2"OTMS), 2.51 (1H, C3'CH), 2.21 (6H, C3'N(CH₃)₂), 1.64, 1.16 (2H, C4'CH₂), 3.64 (1H, C5'CH), 1.15 (3H, C6'CH₃), 4.90 (1H, C1"CH), 2.34, 1.50 (2H, C2"CH₂), 3.31 (3H, C3"OCH₃), 1.15 (3H, C3"CH₃), 3.14 (1H, C4"CH), 0.15 (9H, 4"OTMS), 4.22 (1H, C5"CH, 1.21 (3H, C6"CH₃).

¹³Cnmr (125 MHz, CDCl₃), d: 175.8 (C=O), 45.3 (C2), 16.0 (C2 Me), 78.0 (C3), 39.5 (C4), 9.7 (C4 Me), 78.8 (C5), 79.1 (C6), 20.1 (C6 Me), 54.0 (6OMe), 38.2 (C7), 28.7 (C8), 18.9 (C8 Me), 179.5 (C9, C=N), 33.1 (C10), 14.8 (C10 Me), 70.2 (C11), 73.9 (C12), 16.1 (C12 Me), 76.7 (C13), 21.2 (C14), 10.5 (C15), 163.4 (C16), 25.5, 18.4 (C17CH₃), 102.5 (C1'), 73.3 (C2'), 1.0 (C2'OSi(CH₃)₃), 65.1 (C3'), 41.0 (C3'NMe), 29.5 (C4'), 67.1 (C5'), 22.2 (C6'), 96.1 (C1"), 35.8 (C2"), 73.1 (C3"), 49.7 (C3"OMe), 21.9 (C3"Me), 80.8 (C4"), 0.8 (C4"OSiCHhd 3)₃), 65.1 (C5"), 19.4 (C6") MS (m/z): 946 [M+H]⁺

Example 3(c)

Erythomycin A 6-O-methyl-9-isopropylidene azine

Erythromycin A 2',4"-bis-O-trimethylsilyl-6-O-methyl-9-isopropylidene azine (0.7 g; 0.74 mmol) was dissolved in THF and 1M TBAF/THF solution (3.78 ml; 3.78 mmol) was added. The mixture was stirred at room temperature for 2h. The mixture was evaporated to dryness and the residue partitioned between EtOAc and 5% Aq NaOH solution. The organic layer was separated, dried (MgSO₄) and evaporated in vacuo to give a white solid 0.5 g (84%).

1Hnmr (500 MHz, CDCl₃), d: 2.90 (1H, H2), 1.20 (3H, C2CH₃), 3.75 (1H, C3CH), 1.95 (1H, H4), 1.08 (C4CH₃), 3.66 (1H, C5CH), 1.41 (3H, C6CH₃), 2.96 (1H, 6OMe), 1.62, 1.54 (2H, C7CH₂), 3.89 (1H, C8CH), 1.01 (3H, C8CH₃), 2.67 (1H, C10 CH, 1.19 (3H, C10CH₃), 3.76 (1H, C11CH), 5.62 (11OH) 1.16 (3H, C12CH₃), 3.38 (12H), 5.11 (1H, C13CH), 1.95, 1.48 (2H, C14CH₂), 0.84 (3H, C15CH₃), 2.06, 1.95 (C17CH₃), 4.46 (1H, C1'CH), 3.24 (1H, C2'CH), 2.50 (1H, C3'CH), 2.35 (6H, C3'N(CH₃)2), 1.73, 1.24 (2H, C4'CH₂), 3.50 (1H, C5'CH), 1.23 (3H, C6'CH₃), 4.93 (1H, C1"CH), 2.35, 1.58 (2H, C2"CH₂), 3.33 (3H, C3"OCH₃), 1.25 (3H, C3"CH₃), 3.02 (1H, C4"CH), 4.01 (1H, C5"CH), 1.29 (3H, C6"CH₃).

¹³Cnmr (125 MHz, CDCl3), d: 175.4 (C=O), 45.1 (C2), 16.1 (C2 Me), 78.4 (C3), 39.0 (C4), 9.2 (C4 Me), 80.3 (C5), 78.8 (C6), 20.0 (C6 Me), 50.9 (6OMe), 37.8 (C7), 28.8 (C8), 19.0 (C8 Me), 179.5 (C9, C=N), 33.0 (C10), 14.9 (C10Me), 70.3 (C11), 74.0 (C12), 16.0 (C12 Me), 76.9 (C13), 21.1 (C14), 10.6 (C15), 163.6 (C16), 25.5, 18.5 (C17CH₃), 102.6 (C1'), 71.1 (C2'), 65.5 (C3'), 40.3 (C3'NMe), 29.2 (C4'), 68.5 (C5'), 21.4 (C6'), 96.0 (C1"), 34.9 (C2"), 72.7 (C3"), 49.5 (C3"OMe), 21.5 (C3"Me), 77.9 (C4"), 65.7 (C5"), 18.6 (C6").

MS (m/z): 802 [M+H]⁺

Example 3 (d)

Erythromycin A 6-O-methyl-9-oxime

Erythromycin A 6-O-methyl-9-isopropylidene azine (100 mg; 0.125 mmol) was dissolved in i-PrOH (5 ml) and 50% Aq NH₂OH (5 ml) and AcOH (2 drops) were added. The mixture was heated at reflux overnight. The resulting solution was evaporated in vacuo and the residue was partitioned between EtOAc and 5% NaOH. The organic layer was separated, washed with brine, dried (MgSO₄) and evaporated in vacuo. The white residue was slurried with ACN, the suspended solid was filtered off and the filtrate evaporated to dryness to yield a white solid 89 mg (94%).

MS (m/z): 763 [M+H]⁺

Example 3(e)
6-O-methyl Erythromycin A

Erythromycin A 6-O-methyl-9-oxime (35 mg; 0.046 mmol) from the above example was dissolved in i-PrOH (2 ml) and H₂O (3 ml) and sodium bisulfite (33 mg; .0174 mmol; 3.8eq) was added. The mixture was heated at reflux for 6 h, then evaporated to dryness, partitioned between ethyl acetate and 5% NaOH. The organic layer was dried (MgSO₄) and evaporated to give a white solid 25 mg (74%).

¹Hnmr (500 MHz, CDCl₃), d: 2.89 (1H, H2), 1.20 (3H, C2CH₃), 3.77 (1H, C3CH), 1.92 (1H, H4), 1.10 (C4CH₃), 3.67 (1H, C5CH), 1.41 (3H, C6CH₃), 3.04 (3H, C6OCH₃), 1.85, 1.72 (2H, C7CH₂), 2.59 (1H, C8CH), 1.13 (3H, C8CH₃), 3.00 (1H, C10CH), 1.13 (3H, C10CH₃), 3.77 (1H, C11CH), 1.12 (3H, C12CH₃), 5.05 (1H, C13CH), 1.92, 1.47 (2H, C14CH₂), 0.84 (3H, C15CH₃), 4.44 (1H, C1'CH), 3.19 (1H, C2'CH), 2.42 (1H, C3'CH), 2.29 (6H, C3'N(CH₃)2), 1.66, 1.22 (2H, C4'CH₂), 3.49 (1H, C5'CH), 1.23 (3H, C6'CH₃), 4.93 (1H, C1"CH), 2.37, 1.59 (2H, C2"CH₂), 3.33 (3H, C3"OCH₃), 1.25 (3H, C3"CH₃), 3.03 (1H, C4"CH), 4.01 (1H, C5"CH), 1.31 (3H, C6"CH₃).

¹³Cnmr (125 MHz, CDCl₃), d: 175.8 (C=O), 45.1 (C2), 15.9 (C2 Me), 78.4 (C3), 39.2 (C4), 9.1 (C4Me), 80.8 (C5), 78.4 (C6), 19.7 (C6Me), 39.3 (C7), 45.2 (C8), 18.0 (C8Me), 220.9 (C9, C=O), 37.2 (C10), 12.3 (C10 Me), 69.1 (C11), 74.3 (C12), 15.9 (C12Me), 76.6 (C13), 21.0 (C14), 10.6 (C15), 102.7 (C1'), 71.0 (C2'), 65.6 (C3'), 40.3 (C3'NMe), 28.9 (C4'), 68.7 (C5'), 21.5 (C6'), 96.1 (C1"), 34.9 (C2"), 72.7 (C3"), 49.5 (C3"OMe), 21.4 (C3"Me), 77.9 (C4"), 65.8 (C5"), 18.7 (C6").

MS (m/z): FAB 748 [M+H]⁺
MS (m/z): 748 [M+H]⁺

Example 4 (a)
Erythromycin A 9-cyclohexylidene azine

Erythromycin A hydrazone (10 g; 13.37 mmol) from Example 1(a) was suspended in MeCN (70 ml) and IPCH ketal (10 ml) and formic acid (2 ml) were added. The resulting mixture was stirred at ambient temperature overnight The solution was basifzfed to pH>9 with 5% NaOH, the organic layer was separated, dried (MgSO₄) and evaporated in vacuo to give a white solid (10.925 g; 99%).

¹Hnmr (500 MHz, CDCl₃), d: 2.92 (1H, H2), 1.18 (3H, C2CH₃), 4.03 (1H, C3CH), 2.06 (1H, H4), 1.11 (C4CH₃), 3.62 (1H, C5CH), 1.47 (3H, C6CH₃), 2.94 (1H, 6OH), 1.69, 1.51 (2H, C7CH₂), 3.43 (1H, C8CH), 1.02 (3H, C8CH₃), 2.73 (1H, C10CH), 1.21 (3H, C10CH₃), 3.72 (1H, C11CH), 5.32 (1H, 11H), 1.13 (3H, C12CH₃), 3.19 (1H, 12H), 5.14 (1H, C13CH), 1.91, 1.47 (2H, C14CH₂), 0.83 (3H, C15CH₃), 4.45 (1H, C1'C1'CH), 3.25 (1H, C2'CH), 2.52 (1H, C3'CH), 2.35 (6H, C3'N(CH₃)₂), 1.73, 1.25 (2H, C4'CH₂), 3.51 (1H, C5'CH), 1.22 (3H, C6'CH₃), 4.92 (1H, C1"CH), 2.34, 1.58 (2H, C2"CH₂), 3.31 (3H, C3"OCH₃), 1.24 (3H, C3"CH₃), 3.03 (1H, C4"CH), 2.24 (9H, 4"OH), 4.02 (1H, C5"CH), 1.30 (3H, C6"CH₃), 2.45, 2.27, 2.33, 1.72, 1.64, 1.59 (cyclohexyl CH₂).

¹³Cnmr (125 MHz, CDCl3), d: 174.7 (C=O), 44.6 (C2), 16.3 (C2 Me), 80.2 (C3), 38.5 (C4), 9.3 (C4Me), 83.3 (C5), 75.2 (C6), 27.0 (C6Me), 38.5 (C7), 29.2 (C8), 18.7 (C8Me), 178.5 (C9, C=N), 33.0 (C10), 14.2 (C10 Me), 70.8 (C11), 74.3 (C12), 16.1 (C12Me), 76.7 (C13), 21.0 (C14), 10.6 (C15), 102.7 (C1'), 71.1 (C2'), 65.6 (C3'), 40.3 (C3'NMe), 29.2 (C4'), 68.5 (C5'), 21.5 (C6'), 96.3 (C1"), 35.2 (C2"), 72.7 (C3"), 49.4 (C3"OMe), 21.3 (C3"Me), 77.9 (C4"), 65.6 (C5"), 18.6 (C6"), 168.6 (C1"'), 35.6, 28.3, 27.3, 26.2, 25.7 (cyclohexyl CH₂).

MS (m/z): 828 [M+H]⁺

Example 4(b)
Erythromycin A 2',4"-bis-O-trimethylsilyl-9-cyclohexylidene azine Erythromycin A 9-cyclohexylidene azine (2.0 g; 2.42 mmol) was dissolved in MeCN (40 ml) and HMDS (20 g) was added. The mixture became immediately cloudy, and was stirred at ambient temperature over the weekend. The resulting mixture was basified with 5% NaOH, the organic layer was separated, dried (MgSO₄) and evaporated in vacuo to give a white solid 2.065 g; 88%).

¹Hnmr (500 MHz, CDCl₃), d: 2.88 (1H, H2), 1.17 (3H, C2CH₃), 4.19 (1H, C3CH), 1.97 (1H, H4), 1.11 (C4CH₃), 3.61 (1H, C5CH), 1.45 (3H, C6CH₃), 2.79 (1H, 6OH), 1.70, 1.50 (2H, C7CH₂), 3.48 (1H, C8CH), 1.03 (3H, C8CH₃), 2.76 (1H, C10 CH), 1.23 (3H, C10CH₃), 3.73 (1H, C11CH), 5.29 (1H, 11OH), 1.18 (3H, C12CH₃), 3.21 (1H, 12H), 5.12 (1H, C13CH), 1.93, 1.50 (2H, C14CH₂), 0.86 (3H, C15CH₃), 4.39 (1H, C1'CH), 3.17 (1H, C2'CH), 0.11 (9H, 2"OTMS), 2.54 (1H, C3'CH), 2.23 (6H, C3'N(CH₃)₂), 1.66, 1.19 (2H, C4'CH₂), 3.63 (1H, C5'CH), 1.17 (3H, C6'CH₃), 4.88 (1H, C1"CH), 2.36, 1.50 (2H, C2"CH₂), 3.31 (3H, C3"OCH₃), 1.15 (3H, C3"CH₃), 3.17 (1H, C4"CH), 0.15 (9H, 4"OTMS), 4.24 (1H, C5"CH), 1.23 (3H, C6"CH₃), 2.44, 2.28, 2.34, 1.77, 1.63 (cyclohexyl CH₂).

¹³Cnmr (125 MHz, CDCl₃), d: 175.4 (C=O), 44.7 (C2), 16.1 (C2 Me), 79.8 (C3), 39.5 (C4), 9.7 (C4Me), 81.3 (C5), 75.5 (C6), 27.2 (C6Me), 39.2 (C7), 29.1 (C8), 18.7 (C8Me), 178.3 (C9, C=N), 33.1 (C10), 14.2 (C10Me), 70.9 (C 11), 74.4 (C12), 16.1 (C12Me), 76.7 (C13), 21.1 (C14), 10.7 (C15), 102.6 (C1'), 73.5 (C2'), 1.0 (C2'OSi(CH₃)₃), 65.2 (C3'), 41.0 (C3'NMe), 29.8 (C4'), 67.6 (C5'), 21.8 (C6'), 96.7 (C1"), 36.0 (C2"), 73.2 (C3"), 49.7 (C3"OMe), 22.2 (C3"Me), 81.0 (C4"), 0.9 (C4'OSi(CH₃)₃), 65.0 (C5"), 19.4 (C6"), 168.2 (C1"'), 35.6, 28.4, 27.3, 26.2, 25.8 (cyclohexyl CH₂).

MS (m/z): 972 [M+H]⁺

Example 4(c)
Erythromycin A 2',4"-bis-O-trimethylsilyl-6-O-methyl-9-cyclohexylidene azine Erythromycin A 2',4"-bis-O-trimethylsilyl-9-cyclohexylidene azine (1.0 g; 1.02 mmol) was dissolved in a 1:1 mixture of THF/DMSO (10 ml) and cooled to 5° C. Methyl iodide (0.36 ml; 5.82 mmol) and KOH (0.217 g; 3.88 mmol) were added and the mixture was stirred at 5° C. for 90 min. The reaction was quenched by the addition of aq methylamine (1 ml). Saturated NaCl was added and the resulting mixture extracted with TBME. The organic layer was washed with saturated NaCl solution then dried (MgSO₄) and evaporated in vacuo to give a white solid (0.85 g; 84%).

MS (m/z): 986 [M+H]⁺
1Hnmr (500 MHz, CDCl3) 5.57 (11OH). 5.10 (C13CH), 4.90 (C1"H), 4.42 (C1'CH) 4.22 (C5"CH) 4.09 (C3CH), 3.30 (C3"OMe), 2.96 (C6OMe), 2.90 (H2), 2.22 (C3'NMe2), 2.44, 2.28, 2.34, 1.77, 1.63 (cyclohexyl CH2), 1.49 (C14CH2), 1.40 (C6 Me), 1.21 (C6"CH3), 1.20 (C10CH3), 1.19 (C12Me), 1.18 C2 Me), 1.15 (C3"Me), 1.05 (C4CH3), 1.01 (C8CH3), 0.85 (Cl5CH3), 0.10 (2'OTMS), 0.15 (4"OTMS) 13Cnrnr (125 MHz, CDC13) 175.9 (C=O), 45.5 (C2), 79.0 (C3), 39.5 (C4), 9.5 (C4 Me), 80.9 (C5), 79.0 (C6), 19.4 (C6Me), 39.2 (C7), 45.5 (C8), 19.4 (C8Me), 36.0 (C10), 14.9 (C10Me), 70.2 (C11), 73.9 (C12), 16.1 (C12Me), 76.6 (C13), 21.0 (C14), 10.6 (C15), 102.6 (C1'), 73.3 (C2'), 65.1 (C3'), 40.7 (C3'NMe), 29.5 (C4'), 67.2 (C5'), 21.4 (C6'), 96.0 (C1"), 35.8 (C2"), 73.9 (C3"), 78.0 (C4"), 65.1 (C5"), 18.8 (C6")

Example 4(d)
Erythromycin A 6-O-methyl-9-cyclohexylidene azine

Erythromycin A 2',4"-bis-O-trimethylsilyl-6-O-methyl-9-cyclohexylidene azine (4 g; 4.06 mmol) was dissolved in THF (40 ml) and 1 M TBAF/THF solution (20.70 ml; 20.70 mmol) was added. The mixture was stirred at room temperature for 2h. The mixture was evaporated to dryness and the residue partitioned between EtOAc and 5% Aq NaOH solution. The organic layer was separated, dried (MgSO$_4$) and evaporated in vacuo to give a white solid 2.9 g (85%).
MS (m/z): FAB 842 [M+H]$^+$ Example 4(e)
6-O-methyl Ery A Erythromycin-6-O-methyl-9-cyclohexylidene azine (200 mg; 238 mmol) was dissolved in i-PrOH (10 nmL) and 50%aq NH$_2$OH (10 mL) and AcOH (4 drops) were added. The mixture was heated at reflux overnight. The resulting solution was evaporated to dryness and the residue was partitioned between EtOAc and 5% NaOH. The organic layer was separated and dried (MgSO$_4$) and evaporated in vacuo giving erythromycin A 6-O-methyl-9-oxime as an off-white solid 146 mg (81%) Spectral and chromatographic data were identical with Example 3d. The oxime (50 mg; 0.0657 mmol) was dissolved in IPA (2 mL) and H$_2$O (3 mL) and sodium bisulfite (47 mg; 0.249 mnmol; 3.8 eq) was added. The mixture was heated at reflux overnight then evaporated in vacuo and partitioned between EtOAc and 5% NaOH. The organic layer was separated, dried (MgSO4) and evaporated in vacuo to give a white solid 55 mg.

1Hnmr (500 MHz, CDCl$_3$), d: 2.89 (1H, H2), 1.20 (3H, C2CH$_3$), 3.77 (1H, C3CH), 1.92 (1H, H4), 1.10 (C4CH$_3$), 3.67 (1H, C5CH), 1.41 (3H, C6CH$_3$), 3.04 (3H, C6OCH$_3$), 1.85, 1.72 (2H, C7CH$_2$), 2.59 (1H, C8CH), 1.13 (3H, C8CH$_3$), 3.00 (1H, C10CH), 1.13 (3H, C10CH$_3$), 3.77 (1H, C11CH), 1.12 (3H, C12CH$_3$), 5.05 (1H, C13CH), 1.92, 1.47 (2H, C14CH$_2$), 0.84 (3H, C15CH$_3$), 4.44 (1H, C1'CH), 3.19 (1H, C2'CH), 2.42 (1H, C3'CH), 2.29 (6H, C3'N(CH$_3$)$_2$), 1.66, 1.22 (2H, C4'CH$_2$), 3.49 (1H, C5'CH, 1.23 (3H, C6'CH$_3$), 4.93 (1H, C1"CH), 2.37, 1.59 (2H, C2"CH$_2$), 3.33 (3H, C3"OCH$_3$), 1.25 (3H, C3"CH$_3$), 3.03 (1H, C4-"CH), 4.01 (1H, C5"CH), 1.31 (3H, C6"CH$_3$). $^{13}$Cnmr (125 MHz, CDCl$_3$), d: 175.8 (C=O), 45.1 (C2), 15.9 (C2 Me), 78.4 (C3), 39.2 (C4), 9.1 (C4Me), 80.8 (C5), 78.4 (C6), 19.7 (C6Me), 39.3 (C7), 45.2 (C8), 18.0 (C8Me), 220.9 3 (C9, C=O), 37.2 (C10), 12.3 (C10Me), 69.1 (C15), 74.3 (C12), 15.9 (C12Me), 76.6 (C13), 21.0 (C14), 10.6 (C15), 102.7 (C1'), 71.0 (C2'), 65.6 (C3'), 40.3 (C3'NMe), 28.9 (C4'), 68.7 (C5'), 21.5 (C6'), 96.1 (C1"), 34.9 (C2"), 72.7 (C3"), 49.5 (C3"OMe), 21.4 (C3"Me), 77.9 (C4"), 65.8 (C5"), 18.7 (C6").
MS (m/z): FAB 748 [M+H]$^+$

We claim:

1. A compound having the formula:

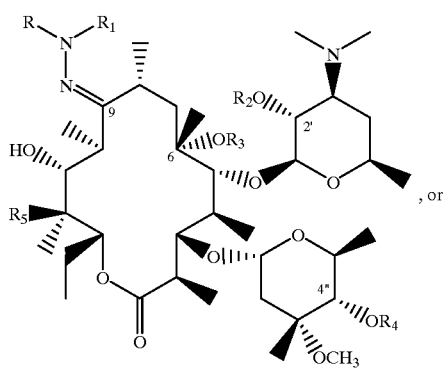

(I)

, or

-continued

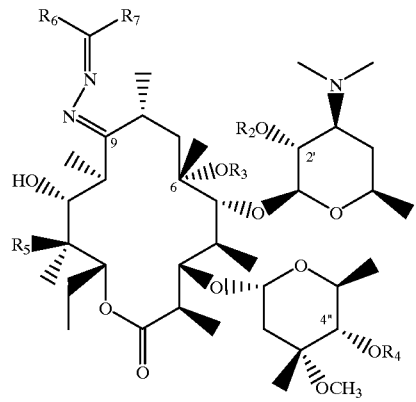

(II)

wherein R and R$_1$ are independently a hydrogen or a nitrogen-protecting group;

R$_2$ and R$_4$ are independently a hydrogen or a hydroxy-protecting group;

R$_3$ is a loweralkyl or an aryl group;

R$_5$ is a hydrogen, hydroxy or a protected hydroxy group; and

R$_6$ and R$_7$ are independently at each occurrence a hydrogen, an alkyl or an aryl group.

2. The compound of Formula I according to claim 1, wherein R and R$_1$ are independently a hydrogen and triisopropylsilyl, R$_2$ and R$_4$ are each trimethylsilyl, R$_3$ is methyl and R$_5$ is hydroxy.

3. The compound of Formula I according to claim 1, wherein R and R$_1$ are independently a hydrogen and N-t-butyldimethylsilyl, R$_2$ and R$_4$ are each trimethylsilyl, R$_3$ is methyl and R$_5$ is hydroxy.

4. The compound of Formula II according to claim 1, wherein R$_6$ and R$_7$ are independently a hydrogen and N-isopropylidene, R$_2$ and R$_4$ are each trimethylsilyl, R$_3$ is methyl and R$_5$ is hydroxy.

5. The compound of Formula II according to claim 1, wherein R$_6$ and R$_7$ are independently a hydrogen and N-cyclohexylidene, R$_2$ and R$_4$ are each trimethylsilyl, R$_3$ is methyl and R$_5$ is hydroxy.

6. A process for preparing a compound of the formula:

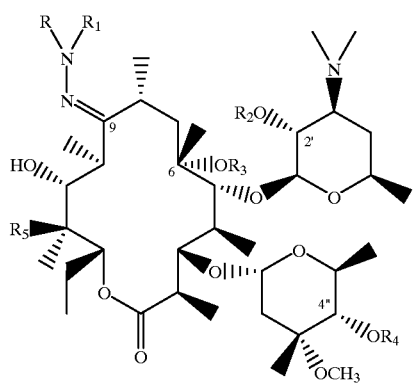

(I)

wherein R and R$_1$ are independently a hydrogen or a nitrogen-protecting group;

R$_2$ and R$_4$ are independently a hydrogen or a hydroxy-protecting group;

$R_3$ is a loweralkyl or aryl group; and
$R_5$ is a hydrogen, hydroxy or a protected hydroxy group; comprising:
a) reacting an erythromycin of the formula:

(II)

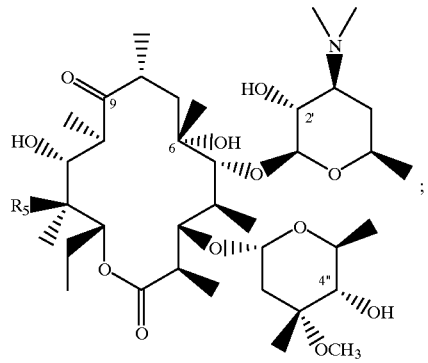

wherein $R_5$ is as defined above, with hydrazine to convert the 9-keto into a corresponding 9-hydrazone erythromycin derivative;
b) protecting the 2'-hydroxy, and optionally the 4"-hydroxy, and the hydrazone nitrogen with hydroxy and nitrogen protecting groups, respectively; and
c) selectively alkylating the 6-hydroxy group.

7. The process according to claim 6, wherein R and $R_1$ are independently a hydrogen and triisopropylsilyl, $R_2$ and $R_4$ are each trimethylsilyl, $R_3$ is methyl and $R_5$ is hydroxy.

8. The process according to claim 6, wherein R and $R_1$ are independently a hydrogen and N-t-butyldimethylsilyl, $R_2$ and $R_4$ are each trimethylsilyl, $R_3$ is methyl and $R_5$ is hydroxy.

9. A process for preparing a compound of the formula:

(II)

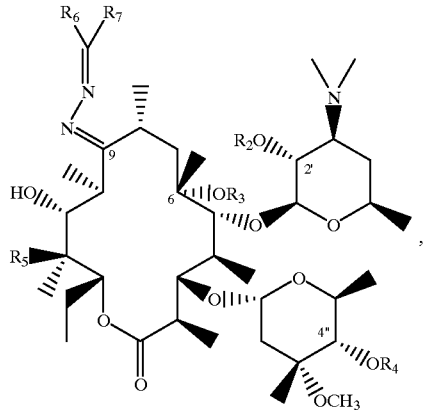

wherein $R_2$ and $R_4$ are independently a hydrogen or a hydroxy-protecting group;
$R_3$ is a loweralkyl or aryl group;
$R_5$ is a hydrogen, hydroxy or a protected hydroxy group; and
$R_6$ and $R_7$ are independently at each occurrence a hydrogen, an alkyl or an aryl group; comprising:
a) reacting an erythromycin of the formula:

(II)

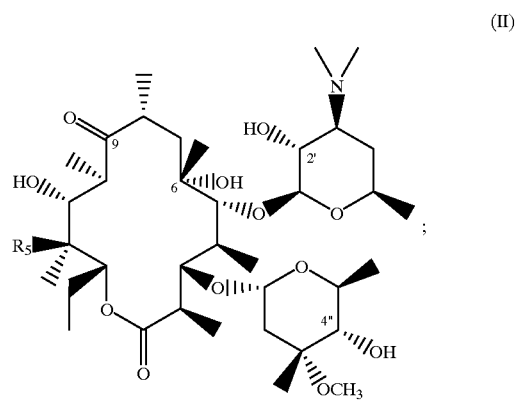

wherein $R_5$ is as defined above, with hydrazine to convert the 9-keto into a corresponding 9-hydrazone erythromycin derivative;
b) reacting the hydrazone from step (a) with a ketone, an aldehyde or an acetal thereof or an orthoformate to produce a corresponding 9-azine erythromycin derivative;
c) protecting the 2'- and optionally the 4"-hydroxy and azine nitrogen with hydroxy and nitrogen protecting groups, respectively; and
d) selectively alkylating the 6-hydroxy group.

10. The process according to claim 9, wherein $R_6$ and $R_7$ are independently a hydrogen and N-isopropylidene, $R_2$ and $R_4$ are each trimethylsilyl, $R_3$ is methyl and $R_5$ is hydroxy.

11. The process according to claim 9, wherein $R_6$ and $R_7$ are independently a hydrogen and N-isopropylidene, $R_2$ and $R_4$ are each trimethylsilyl, $R_3$ is methyl and $R_5$ is hydroxy.

12. The process according to claim 6, wherein the protected hydroxyl and nitrogen groups in the product of step (c) are deprotected to yield the corresponding 6-O-loweralkyl or aryl erythromycin A 9-hydrazone.

13. The process according to claim 9, further comprising deprotecting the product obtained in step (d) with hydroxylamine to afford the corresponding 6-O-loweralkyl or aryl erythromycin A 9-oxime derivative.

14. The process according to claim 9, further comprising:
(a) reacting the compound obtained in step (d) with hydrazine to afford a corresponding 9-hydrazone; and
(b) deprotecting the 9-hydrazone with nitrous acid to afford the corresponding 6-O-loweralkyl or aryl erythromycin A 9-hydrazone.

* * * * *